US006399621B1

(12) United States Patent
Dusza et al.

(10) Patent No.: US 6,399,621 B1
(45) Date of Patent: Jun. 4, 2002

(54) N-METHYL-N-(3-{3-[2-THIENYLCARBONYL]-PYRAZOL-[1, 5-α]-PYRIMIDIN-7-YL}PHENYL)ACETAMIDE AND COMPOSITIONS AND METHODS RELATED THERETO

(75) Inventors: John P. Dusza, Nanuet, NY (US); Andrew S. Tomcufcik, Glen Mills, PA (US); Jay D. Albright, Nanuet, NY (US); Bernard Beer, Cliffside Park, NJ (US)

(73) Assignee: American Cyanamid Company, Madison, NJ (US)

( * ) Notice: Subject to any disclaimer, the term of this patent is extended or adjusted under 35 U.S.C. 154(b) by 0 days.

(21) Appl. No.: 09/636,381

(22) Filed: Aug. 9, 2000

Related U.S. Application Data

(60) Provisional application No. 60/203,163, filed on May 9, 2000, and provisional application No. 60/148,431, filed on Aug. 10, 1999.

(51) Int. Cl.[7] ..................... C07D 409/02; A61K 31/519
(52) U.S. Cl. ........................ 514/258; 544/281
(58) Field of Search ........................... 514/258; 544/281

(56) References Cited

U.S. PATENT DOCUMENTS

| 4,382,938 A | 5/1983 | Kaplan et al. | 424/256 |
| 4,460,592 A | 7/1984 | Kaplan et al. | 424/256 |
| 4,521,422 A | 6/1985 | Dusza et al. | 514/258 |
| 4,626,538 A | 12/1986 | Dusza et al. | 514/258 |
| 4,654,347 A | 3/1987 | Dusza et al. | 514/258 |
| 4,794,185 A | 12/1988 | Rossey et al. | 546/121 |
| 4,808,594 A | 2/1989 | George et al. | 514/300 |
| 4,847,256 A | 7/1989 | Tseng et al. | 514/258 |
| 4,900,836 A | 2/1990 | Tomcufcik et al. | 546/279 |
| 5,538,977 A | 7/1996 | Dusza et al. | 514/258 |
| 5,714,607 A | 2/1998 | Padmanathan | 544/281 |
| 5,891,891 A | 4/1999 | Benincasa | 514/300 |

FOREIGN PATENT DOCUMENTS

WO   WO 99/57101   11/1999

OTHER PUBLICATIONS

Foster, "Developments in CNS Drugs II: Drugs of Tomorrow," SMi Conference, London, UK, May 11–12th, 1999 no copy provided.

*Primary Examiner*—John M. Ford
(74) *Attorney, Agent, or Firm*—Seed Intellectual Property Law Group PLLC

(57) ABSTRACT

N-methyl-N-(3-{3-[2-thienylcarbonyl]-pyrazol-[1,5-α]-pyrimidin-7-yl}phenyl)acetamide, and use of the same as a sedative-hypnotic, anxiolytic, anticonvulsant, and skeletal muscle relaxant agent. Compositions containing N-methyl-N-(3-{3-[2-thienylcarbonyl]-pyrazol-[1,5-α]-pyrimidin-7-yl}phenyl)acetamide, as well as pharmaceutically acceptable salts thereof, are also disclosed.

9 Claims, No Drawings

N-METHYL-N-(3-{3-[2-THIENYLCARBONYL]-PYRAZOL-[1, 5-α]-PYRIMIDIN-7-YL}PHENYL)ACETAMIDE AND COMPOSITIONS AND METHODS RELATED THERETO

CROSS-REFERENCE TO RELATED APPLICATIONS

This application claims the benefit of U.S. Provisional Application No. 60/203,163 filed May 9, 2000, and U.S. Provisional Application No. 60/148,431 filed Aug. 10, 1999.

TECHNICAL FIELD

This invention is directed to N-methyl-N-(3-{3-[2-thienylcarbonyl]-pyrazol-[1,5-α]-pyrimidin-7-yl}phenyl) acetamide which has utility as a sedative or hypnotic agent, as well related compositions and methods.

BACKGROUND OF THE INVENTION

The term "insomnia" is used to describe all conditions related to the perception of inadequate or non-restful sleep by the patient (Dement, *International Pharmacopsychiatry* 17:3–38, 1982). Insomnia is the most frequent complaint, being reported by 32% of the adult population surveyed in the Los Angeles area (Bixler et al, *Amer. Journal of Psychiatry* 136:1257–1262, 1979), and 13% of the population surveyed in San Marino, Italy (Lugaresi et al., *Psychiatric Annals* 17:446–453, 1987). Fully 45% of the surveyed adult population of Alachua County, Fla., reported trouble getting to sleep or staying asleep (Karacan et al., *Social Science and Medicine* 10:239–244, 1976). The prevalence of insomnia has also been shown to be related to the age and sex of the individuals, being higher in older individuals and in females.

Insomnia, if left untreated, may result in disturbances in metabolism and overall body function. Reduced productivity and significant changes in mood, behavior and pyschomotor function. Chronic insomnia is associated with a higher incidence of morbidity and mortality. Traditionally, the management of insomnia includes treatment and/or and/or mitigation of the etiological factors, improving sleep hygiene and the administration of hypnotic agents. The early hypnotic agents, such as barbiturates, while effective, elicited a spectrum of unwanted side effects and longer-term complications. For example, barbiturates have the potential to result in lethargy, confusion, depression and a variety of other residual effects many hours post dosing, as well as having a potential for being highly addictive.

During the 1980's, the pharmaceutical treatment of insomnia shifted away from barbiturates and other CNS depressants toward the benzodiazepine class of sedative-hypnotics. This class of sedative-hypnotic agents showed substantial effectiveness in producing a calming effect which results in sleep-like states in man and animals (Gee et al., *Drugs in Central Nervous Systems*, Horwell (ed.), New York, Marcel Dekker, Inc., 1985, p. 123–147) and had a greater safety margin than prior hypnotics, barbiturates or chloral hydrate (Cook and Sepinwall, *Mechanism of Action of Benzodiazepines*, Costa and Greengard (eds.), New York, Raven Press, 1975, p. 1–28). The therapeutic action of benzodiazepines are believed to be mediated by binding to a specific receptor on benzodiazepine GABA complexes in the brain. As a result of this binding, synaptic transmission is altered at neurons containing the benzodiazepine GABA complex (Clody et al., *Benzodiazepines II*, Rechtschaffen and Kales (eds.), New York, Springer-Verlag, 1989, p. 341–354). The clinical usefulness of different benzodiazepine hypnotics relates largely to their pharmacokinetic differences with regard to this binding and, in particular, to the half-lives of the parent compound and its active metabolites (Finkle, *Benzodiazepines II*, Rechtschaffen and Kales (eds.), New York, Springer-Verlag, 1989, p. 619–628).

As with barbiturates, however, many benzodiazepines also possess side effects that limit their usefulness in certain patient populations. These problems include synergy with other CNS depressants (especially alcohol), the development of tolerance upon repeat dosing, rebound insomnia following discontinuation of dosing, hangover effects the next day, and impairment of psychomotor performance and memory (Cook and Sepinwall, supra; Hartman, *Benzodiazepines II*, Rechtschaffen and Kales (eds.), New York, Springer-Verlag, 1989, p. 187–198; Linnoila and Ellinwood, *Benzodiazepines II*, Rechtschaffen and Kales (eds.), New York, Springer-Verlag, 1989, p. 601–618). Memory impairment, which can include amnesia for events occurring prior to and after drug administration, is of particular concern in the elderly whose cognitive function may already be impaired by the aging process (Ayd, *Benzodiazepines II*, Rechtschatfen and Kales (eds.), New York, Springer-Verlag, 1989, p. 593–600; Finkle, supra; Linnoila and Ellinwood, supra).

More recently, a new class of agents have undergone development. These agents are non-benzodiazepine compounds, which bind selectively to a specific receptor subtype of the benzodiazepine receptor. This receptor selectivity is thought to be the mechanism by which these compounds are able to exert a robust hypnotic effect, while also demonstrating an improved safety profile relative to the non-selective, benzodiazepine class of agents. The first of these agents to be approved by the United States Food and Drug Administration (FDA) for marketing in the United States was Ambien (zolpidem tatrate), which is based on the imidazopyridine backbone (see U.S. Pat. Nos. 4,382,938 and 4,460,592). In addition to Ambien, another compound known as Sonata (zelaphon), which is a pyrazolopyrimidine-based compound, is currently awaiting FDA approval (see U.S. Pat. No. 4,626,538). Other non-benzodiazepine compounds and/or methods for making or using the same have also been reported (see, e.g., U.S. Pat. Nos. 4,794,185, 4,808,594, 4,847,256, 5,714,607, 4,654,347; 5,891,891; 5,538,977).

While significant advances have been made in this field, there is still a need in the art for compounds which are effective as sedative or hypnotic agents generally, particularly in the context of treating insomnia. Such compounds preferably have superior PK profiles in adults and the elderly, a preferable metabolism and excretion pathway, a lower propensity to tolerance, less hangover effects, no additive effects with alcohol and other CNS depressant drugs, and/or a lower propensity for abuse. The present invention fulfills this need and provides further related advantages.

SUMMARY OF THE INVENTION

In brief, the present invention is directed to a compound and the use of the same as a sedative or hypnotic agent. More specifically, the compound of this invention is N-methyl-N-(3-{3-[2-thienylcarbonyl]-pyrazol-[1,5-α]-pyrimidin-7-yl}phenyl)acetamide, which compound has the following structure 1 (referred to herein as "Compound 1" or "1"), including pharmaceutically acceptable salts thereof:

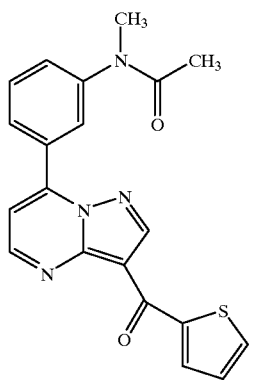

Compound 1

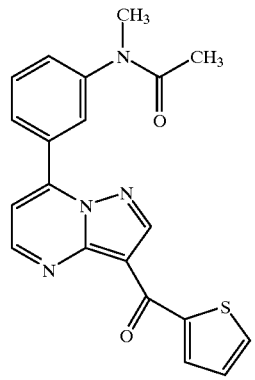

Compound 1

The present invention is also directed to methods for treating a variety of conditions by administering an effective amount of Compound 1 to an animal or subject in need thereof (referred to herein as a "patient"), typically a warm-blooded animal (including a human). Prior to administration, Compound 1 is preferably formulated as a pharmaceutical composition which contains an effective dosage amount of Compound 1 in combination with one (or more) pharmaceutically acceptable carrier(s). Conditions that may be treated by Compound 1, or a pharmaceutical composition containing Compound 1, include any condition which may benefit from administration of agents which possess anxiolytic, anti-anoxic, sleep-inducing, hypnotic, anticonvulsant, and/or skeletal muscle relaxant properties. Such conditions include insomnia specifically, as well as sleep disorders generally and other neurological and psychiatric complaints, anxiety states, vigilance disorders, such as for combating behavioral disorders attributable to cerebral vascular damage and to the cerebral sclerosis encountered in geriatrics, epileptic vertigo attributable to cranial trauma, and for metabolic encephalopathies.

These and other aspects of this invention will be apparent upon reference to the following detailed description. To that end, certain patent and other documents are cited herein to more specifically set forth various aspects of this invention. Each of these documents are hereby incorporated by reference in their entirety.

DETAILED DESCRIPTION OF THE INVENTION

As mentioned above, the present invention is directed to N-methyl-N-(3-{3-[2-thienylcarbonyl]-pyrazol-[1,5-α]-pyrimidin-7-yl}phenyl)acetamide as represented by Compound 1 below, as well as to compositions and methods relating to the same.

Pharmaceutically acceptable salts of Compound 1 are also within the scope of this invention. To this end, Compound 1 may generally be utilized as the free base. Alternatively, Compound 1 may be used in the form of acid addition salts. Acid addition salts of the free base amino compounds of the present invention may be prepared by methods well known in the art, and may be formed from organic and inorganic acids. Suitable organic acids include maleic, fumaric, benzoic, ascorbic, succinic, methanesulfonic, acetic, oxalic, propionic, tartaric, salicylic, citric, gluconic, lactic, mandelic, cinnamic, aspartic, stearic, palmitic, glycolic, glutamic, and benzenesulfonic acids. Suitable inorganic acids include hydrochloric, hydrobromic, sulfuric, phosphoric, and nitric acids. Thus, the term "pharmaceutically acceptable salt" of Compound 1 is intended to encompass any and all acceptable salt forms.

Compound 1 may generally be made by the synthetic procedures disclosed in U.S. Pat. Nos. 4,521,422 and 4,900,836. These patents, particularly U.S. Pat. No. 4,521,422, disclose a genus encompassing certain aryl and heteroaryl [7-(aryl and heteroaryl)-pyrazolo[1,5-a]pyrimidin-3-yl] methanones. Such compounds may generally be classified as "substituted pyrazolopyrimidines" having the following Genus I:

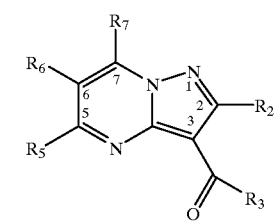

Genus I

In particular, U.S. Pat. No. 4,521,422 discloses that compounds of Genus I may be made by reacting an appropriately substituted pyrazole (a) with an appropriately substituted 3-dimethylamino-2-propen-1-one (b) as represented by the following reaction scheme:

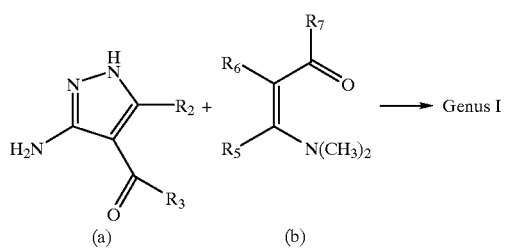

(a)  (b)

The above reaction will yield Compound 1 when $R_2$, $R_5$ and $R_6$ are hydrogen, $R_3$ is thienyl, and $R_7$ is 2-(N(Me)COCH$_3$)-phenyl. A more detailed disclosure directed to the synthesis of Compound 1 is set forth in Example 1.

In another embodiment of the invention, pharmaceutical compositions containing Compound 1 are disclosed. For purpose of administration, Compound 1 is preferably formulated as a pharmaceutical composition. Pharmaceutical compositions of the present invention comprise Compound 1 and a pharmaceutically acceptable carrier, wherein Compound 1 is present in the composition in an amount which is effective to treat the condition of interest. Preferably, the pharmaceutical compositions of the present invention include Compound 1 in an amount from 0.1 mg to 250 mg per dosage depending upon the route of administration, and more typically from 1 mg to 60 mg. Appropriate concentrations and dosages can be readily determined by one skilled in the art.

Pharmaceutically acceptable carriers are familiar to those skilled in the art. For compositions formulated as liquid solutions, acceptable carriers include saline and sterile water, and may optionally include antioxidants, buffers, bacteriostats and other common additives. The compositions can also be formulated as pills, capsules, granules, or tablets which contain, in addition to Compound 1, diluents, dispersing and surface active agents, binders, and lubricants. One skilled in this art may further formulate Compound 1 in an appropriate manner, and in accordance with accepted practices, such as those disclosed in *Remington's Pharmaceutical Sciences*, Gennaro, Ed., Mack Publishing Co., Easton, Pa. 1990.

In another embodiment, the present invention provides a method for treating conditions which benefit from administration of agents which possess anxiolytic, anti-anoxic, sleep-inducing, hypnotic, anticonvulsant, and/or skeletal muscle relaxant properties. Such conditions include insomnia specifically, as well as sleep disorders generally and other neurological and psychiatric complaints, anxiety states, vigilance disorders, such as for combating behavioral disorders attributable to cerebral vascular damage and to the cerebral sclerosis encountered in geriatrics, epileptic vertigo attributable to cranial trauma, and for metabolic encephalopathics.

The methods of this invention include systemic administration of Compound 1, preferably in the form of a pharmaceutical composition. As used herein, systemic administration encompasses both oral and parenteral methods of administration. For oral administration, suitable pharmaceutical compositions include powders, granules, pills, tablets, and capsules as well as liquids, syrups, suspensions, and emulsions. These compositions may also include flavorants, preservatives, suspending, thickening and emulsifying agents, and other pharmaceutically acceptable additives. For parenteral administration, the compounds of the present invention can be prepared in aqueous injection solutions which may contain buffers, antioxidants, bacteriostats, and other additives commonly employed in such solutions.

In a specific embodiment of this invention, an effective amount of Compound 1 is administered to a patient as a sedative or hypnotic agent, particular in the context of treatment of insomnia. Compound 1 has been found to have particular advantageous properties in this context. For example, kinetic binding studies show that Compound 1 binds with high affinity to the same brain "benzodiazepine receptors" as do the benzodiazepines themselves. The binding profile is that of a type 1 benzodiazepine receptor ligand, which typically predicts sedative activity in animals and man. Compound 1 competitively displaces radiolabeled flunitrazepam (IC$_{50}$ of 9.8 nM) from these receptors, and acts as an agonist with comparable efficacy to sedative benzodiazepine ligands since it produces a large increase (65%) in TBPS binding, a compound which is known to bind to a site associated with the benzodiazepine receptor chloride channel. In addition, Ro 15-1788, a highly specific benzodiazepine receptor antagonist, was able to antagonize the decreases in motor activity and to reverse the impairment of grip strength in rats that Compound 1 produces. The desmethyl metabolite of Compound 1 was approximately 74 times less potent in displacing radiolabeled flunitrazepam (IC$_{50}$ of 725 nM) and produced only a small increase (28%) in TBPS binding.

Compound 1 has been also been found to interact directly with the benzodiazepine site on the GABA$_A$ receptor through its ability to inhibit the binding of the selective benzodiazepine ligand [3H]flunitrazepam. Compound 1 displaces [$^3$H]flunitrazepam binding to rat cortex with an IC$_{50}$ value of 9.8 nM. This value lies within the range of affinities of established benzodiazepine ligands tested under similar assay conditions (IC$_{50}$, nM): triaolam (0.5); diazepam (17); zolpidem (26); and flunitrazepam (114). The inhibition of [$^3$H]flunitrazepam binding to rat cortex membranes by compound 1 indicates binding to more than one class of sites (Hill co-efficient=0.6), consistent with the established identity of multiple benzodiazepine receptors. When [$^3$H]flunitrazepine binding to rat cerebellum membranes was examined, compound 1 inhibited with an IC$_{50}$ value of 2 nM and a Hill co-efficient of 0.9. Taken together, these results are consistent with compound 1 binding selectively to type I benzodiazepine sites. Type I benzodiazepine ligands have been shown to have a more specific and potent sedative action in animals and in man.

A further index of activity at the benzodiazepine site on the GABA$_A$ receptor is the ability of Compound 1 to increase the binding of [$^{35}$S] t-butylbicyclophosphorothionate (TBPS) to rat cortex membranes. TBPS binds to a site on the GABA$_A$ receptor which is closely associated with the chloride channel, and an increase in TBPS binding correlates with increased activation of the chloride conductance (i.e., enhanced GABA$_A$ receptor function). Compounds which act as agonists at the benzodiazepine site increase TBPS binding to varying degrees, which reflects their relative efficacies. Compound 1 gave an E$_{max}$ of 65% (maximum enhancement of TBPS binding over the concentration range employed). This compares with the following values for other henzodiazepine ligands obtained under similar assay conditions (E$_{max}$, %): diazepam (55), triazolam (78); flurazepam (71). The value for Compound 1 predicts potent sedative activity, since it falls within the range of values observed for other benzodiazepine ligands which have sedative properties in animals and man.

Benzodiazepine hypnotics produce dose-related decreases in motor activity in many species of animals. In addition, benzodiazepines decrease muscle tone and impair coordinated motor movement. Such effects in animals have been used as preclinical indicators of the sedative potential of drugs when administered to man (Bixler et al., *Amer. Journal of Psychiatry* 136:1257–1262, 1979). Although not a benzodiazepine compound, Compound 1 demonstrates many of the same chemical properties and physiological effects as this class of compounds.

The sedative effects of Compound 1 were measured in rats using a panel of standard tests which monitor the effects of drugs on motor activity, muscle relaxation and motor coordination. The $ED_{50}$ for a decrease in motor activity as measured in an activity meter was 1.2 mg/kg p.o. (unless stated otherwise, all dosings were given orally). The $ED_{50}$ for the muscle relaxant effects of Compound 1, as measured in the inclined screen grip strength test, was 2.7 mg/kg. Similarly, an $ED_{50}$ of 3.0 mg,/kg was noted for the rod walking test, which measures coordinated motor ability. These data place Compound 1 as approximately equipotent with triazolam and more potent than zolpidem and flurazepam. The major desmethyl metabolite of Compound 1, however, did not show sedative effects in these tests.

The sedative actions of Compound 1 was found to be mediated through the benzodiazepine site on the $GABA_A$ receptor by studies employing the selective benzodiazepine site antagonist Ro 15-1788. This latter compound is well characterized as a competitive antagonist at the benzodiazepine site, which can reverse the effects of benzodiazepine site agonists. The effects of 3.1 mg/kg Compound 1 (p.o.) on locomotor activity and in the inclined screen test were reversed by co-treatment with 10 mg/kg Ro 15-1788 (i.p.), confirming that these effects are mediated through the benzodiazepine site.

Compound 1 produced dose-related increases in sleep duration in rats, with a minimum effective dose of 2.0 mg/kg. EEG studies in squirrel monkeys indicate that 4.0 mg/kg of this compound given i.m. caused changes in the EEG power spectrum similar to those seen for the benzodiazepine sedative-hypnotic agents (i.e., a relative decrease in alpha activity and an increase in beta activity).

Vigilance tests based on reaction time measurements in monkeys measure drug induced slowing of responses and decreases in attentional or cognitive processes. Squirrel monkeys were trained to respond to a visual trigger by bar pressing for a food reward. Compound 1 (>1 mg/kg) delivered orally one hour before testing produced dose related decrements in both the accuracy and latency of the responses, results which are similar to those caused by the benzodiazepine sedative-hypnotics.

At low dose levels, the benzodiazepines and barbiturate sedative-hypnotics produce reliable reductions in symptoms of anxiety in man, and these effects have been correlated with that of the earlier induction of sleep in insomniac patients. In addition, the anxiolytic effects are highly correlated with the effects of the same drugs on two well-established behavioral models of conflict situations in rats and monkeys. The effects of Compound 1 on these conflict models are described below.

The Thirsty Rat conflict Procedure involves rats which are deprived of water for 48 hours. They are then given brief electrical shocks following each 20th lick of a drinking tube. These shocks create a "conflict situation" which results in a marked decrease in licking (drinking) behavior. Oral dosing with 0.3 mg/kg of Compound 1 resulted in a 100% increase in the number of shocks accepted by the treated rats compared to rats in the control groups which received only the dosing vehicle. Again, the major desmethyl inetabolite of Compound 1 at a dose of 12 mg/kg was without effect in this conflict model.

The Squirrel Monkey Conflict Procedure involves monkeys which are initially trained to press a bar to receive a food reward. In later sessions the animals were given occasional electrical shocks following randomly selected bar presses. These animals responded to the conflict situation by substantially lowering their levels of bar-pressing activity. Following an oral dose of 2.0 mg/kg of Compound 1 the monkeys showed a 100% increase above their baseline responses to the conflict situation. This increase in conflict response reflects the anxiolytic effects of the drug. The increase drops off at 4.0 mg/kg, which may be due to a subtle sedative effect of the compound which begins developing in this dose range. The inverted-U shaped dose-response function described above for Compound 1 is consistent with the profile of other sedative-hypnotic drugs of the benzodiazepine-ligand class, and reflects the sedative properties of these drugs (Cook and Sepinwall, supra).

Benzodiazepine sedative-hypnotic agents are potent anticonvulsants in animals, and are used clinically for the treatment of status epilepticus. Oral doses of Compound 1 were effective in blocking convulsions in rats which resulted from injections of agents know to induce convulsion (see Table 1 below). In addition, orally administered Compound 1 was effective in blocking convulsions induced by a 150 mA, 60 Hz electrical shock delivered transcorneally for 0.3 seconds ($ED_{50}$ of 5.5 mg/kg). The anticonvulsant potency of Compound 1, as determined by all five of these methods, is less than that of triazolam and greater than that of flurazepam.

TABLE 1

Effects of Oral Compound 1 in Preventing Convulsion

| Convulsion Inducer | $ED_{50}$Compound 1 mg/kg |
|---|---|
| Pentylenetetrazol (iv) | 2.5 |
| Bicuculline (iv) | 2.3 |
| Picrotoxin (sc) | 1.9 |
| Strychnine (sc) | 4.4 |

Administration of benzodiazopines to animals and to man for periods of several weeks can result in a tolerance to their sedative effects (Finkle, supra). In order to assess tolerance to Compound 1, its effects were tested on rat motor activity, and on grip strength using the inclined screen procedures after single and repeated administrations. The results of these studies were then compared to results gathered from rats which had received similar dosings of triazolam. Animals given daily treatment of Compound 1 for four days showed an increase in the $ED_{50}$ (from 2.4 to 14.5 mg/kg when tested for motor activity, and 2.6 to 18.3 mg/kg when tested for grip strength on the fourth day of dosing. This increased tolerance to the Compound 1, while statistically significant, was much less than that caused by triazolam when measured using the same procedures. For triazolam, the $ED_{50}$s for activity and grip strength increased from 3.9 and 5.1 mg/kg, respectively, to values greater than 100 mg/kg after only four days of treatment. The sedative effects of triazolam showed complete tolerance, that is, doses of up to 100 mg/kg were now without sedative activity. Because tolerance to the sedative effects of benzodiazepines may play a role in their abuse and/or addiction liability, the results of these animal studies suggest that Compound 1 may possess a lessened abuse liability compared to the benzodiazepine class of sedative-hypnotics.

Benzodiazepines and barbiturate sedative-hypnotics produce a profound potentiation of the deleterious effects of ethanol (ETOH) in man and animals (Ayd, supra). Intraperitoneal ETOH alone, when administered to rats at a dose of 3.2 g/kg, produces a reliable loss of righting response. The loss of righting response caused by ETOH can be used to measure the possible interaction of ETOH with test drugs. This is done by delivering the ETOH and a test drug sequentially, and determining the Minimum Effective Dose of test drug which will potentiate the time that ETOH produces the loss of righting response. The ETOH Liability Index for a drug can be determined by calculating the ratio of (1) the $ED_{50}$ of the test drug to decrease motor activity (a measure of sedation) to (2) the Minimum Effective Dose (MED) of the test drug too potentiate the time for ETOH-induced loss of righting response.

ETOH Liability Indices were determined experimentally for Compound 1, flurazepam and triazolam by intraperitoneally delivering ETOH (3.2 g/kg) to the animals 60 minutes after dosing with each test drug (see Table 2 below).

TABLE 2

Estimation of ETOH Liability Indices

| Compound | Decrease in Motor Activity ($ED_{50}$ mg/kg) | Minimum Effective Dose (MED mg/kg) | ETOH Liability Index |
|---|---|---|---|
| Compound 1 | 1.2 | 2.5 | 0.48 |
| Flurazepam | 24.9 | 5.0 | 4.98 |
| Triazolam | 1.6 | .08 | 20 |

As mentioned previously, all of these compounds produced dose-related decreases in motor activity. Triazolam and flurazepam resulted in a significant potentiation of the deleterious effects of ETOH, and these effects occurred at doses well below those required to produce decreases in motor activity. Compound 1 also potentiated the ETOH-induced loss of righting response, but, in contrast to triazolam and flurazepam, this potentiation required doses that were greater than those required for decreases in motor activity. On the basis of this analysis, Compound 1 has ≧10 times less ETOH liability as compared to triazolam and flurazepam.

The important observation that Compound 1 causes very little potentiation of ETOH was extended by determining a Hangover Liability Index, the measure of the ability of the drug to potentiate ETOH 24 hours after administration (see Table 3 below). Sedative-hypnotic agents have been reported to produce drowsiness, confusion and other side effects in man on the day following the normal overnight use of these compounds. The ability of a drug to potentiate an ETOH effect when the ETOH is delivered 24 hours after dosing suggests that the compound remains pharmacologically active at that time and therefore might produce next-day hangover effects in man.

TABLE 3

Estimation of Hangover Liability Indices

| Compound | Hangover Liability Index |
|---|---|
| Compound 1 | 0.0 |
| Flurazepam | 2.5 |
| Triazolam | 10 |

Compound 1 failed to potentiate ETOH that was delivered 24 hours after the drug treatment. However, both triazolam and flurazepam significantly potentiated the effects of ETOH given 24 hours after dosing, and caused this potentiation at doses below those which are required to produce effects on motor activity. This comparison suggests that, unlike the benzodiazepine sedative-hypnotics, Compound 1 will not produce next-day hangover effects in man.

The Benzodiazepines and barbiturates have been shown to produce partial amnesia in man and animals. This effect can be studied in rats by the one-trial passive avoidance test. In this test an undrugged, naive rat is given an electric shock when it moves from the illuminated side to the darkened side of a two-compartment chamber. When tested for recall of this training 24 hours later, a placebo-injected animal will show excellent recall of the aversive training, and thus a high latency time for entering the darkened side. Amnestic agents delivered on the second day result in significantly shorter latencies of animal movement into the darkened side.

It is possible to calculate an Amnestic Liability Index (ratio of $ED_{50}$ for decreased motor activity to the MED to produce amnesia) similar to the ETOH Liability index described above for Compound 1 and other agents (see Table 4 below). Compound 1 has a small amnestic effect compared to triazolam or flurazepam.

TABLE 4

Estimation of Amnestic Liability Indices

| Compound | Amnestic Liability Index |
|---|---|
| Compound 1 | 0.15 |
| Flurazepam | 3.1 |
| Triazolam | 1.6 |

The following example is offered by way of illustration, not limitation.

EXAMPLE

Synthesis of Compound 1

Compound 1 of this invention may be made according to the following reaction scheme:

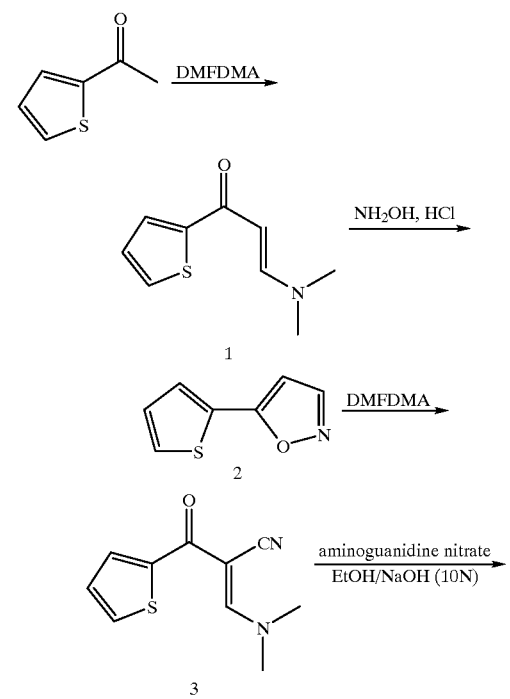

-continued

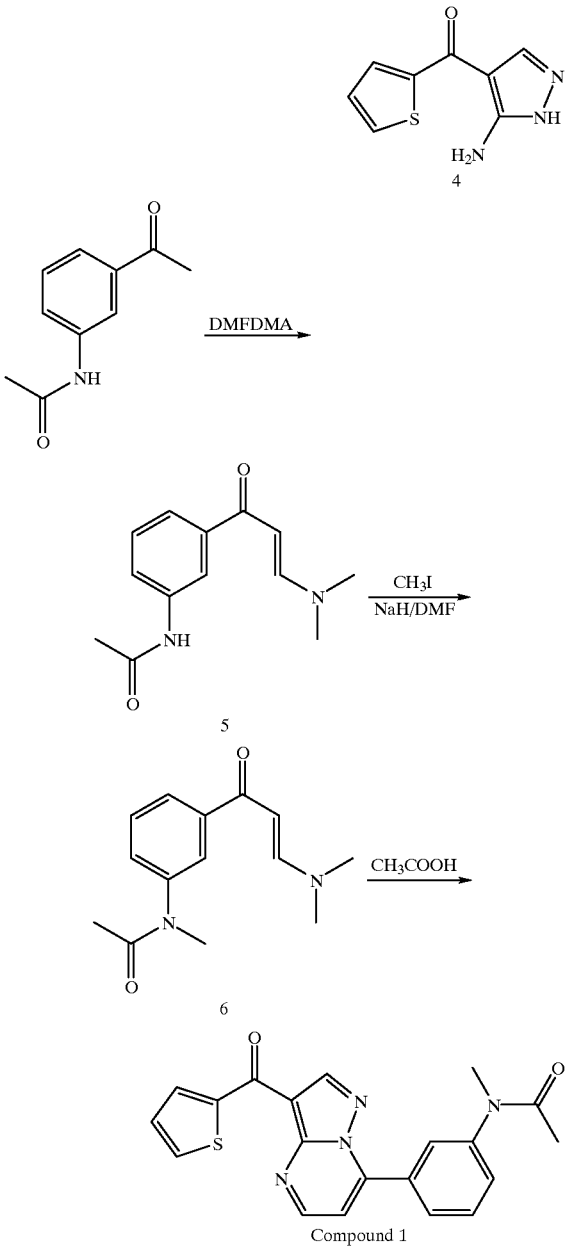

Compound 1

β-Dimethylamino-1-(2-thienyl)-2-propen-1-one (1)

A mixture of 2-acetylthiophene (10.0 g, 80 mmol) (Aldrich) and dimethylformamide dimethyl acetal (15 g, 126 mmol) is refluxed under nitrogen for 3 hrs, The reaction mixture is cooled and hexane (300 mL) added. The solid is collected by filtration to yield product (1) as an orange solid (9.1 g, 50 mmol, 63%).

5-(2-Thienyl)isoxazole (2)

A mixture of β-dimethylamino-1-(2-thienyl)-2-propen-1-one (1) (18.1 g, 100 mmol) and hydroxylamine hydrochloride (7.0 g, 101 mmol) in anhydrous methanol (100 mL) is refluxed under nitrogen for 2 hrs. The reaction mixture is cooled, concentrated and partitioned between water and dichloromethane. The dichloromethane layer is dried with anhydrous sodium sulfate, filtered and concentrated to yield product (2) as a dark yellow-orange oil (14.7 g, 97 mmol, 97%).

α-[(Dimethylamino)methylene]-β-oxo-2-thiophenepropanenitrile (3)

A mixture of 5-(2-thienyl)isoxazole (2) (13.0 g, 86 mmol) and dimetbylformamide dimethyl acetal (25 mL, 188 mmol) is refluxed under nitrogen for 8 hrs. Solid precipitates from the reaction mixture. Hexane is added to the reaction mixture and the solid is collected by filtration, giving product (3) as an orange solid (13.5 g, 65 mmol, 76%).

(3-Amino-1H-pyrazol-4-yl)-2-thienylmethanone (4)

To a mixture of aminoguanidine nitrate (17.1, 125 mmol) and α-[(dimethylamino)methylene]-β-oxo-2-thiophenepropanenitrile (3) (20.6 g, 100 mmol) in commercial absolute ethanol (120 mL) is added 10N NaOH (5 g of solid NaOH in 12.5 mL of water). The reaction mixture is refluxed for 6 hrs and the solvents removed at reduced pressure on a rotary evaporator. Water (250 mL) is added and an initial precipitate forms and is filtered (13.3 g, 68.8 mmol, 69%). On further standing the aqueous layer deposits an additional quantity of the titled compound (3.42 g, 17.7 mmol, 18%), yielding product (4) as a tan solid (total 16.72 g, 86.5 mmol, 87%).

N-[3-[3-(Dimethylamino)-1-oxo-2-propenyl]-phenyl]-acetamide (5)

A mixture of 3-acetamidoacetophenone (30 g, 169 mmol) and dimethylformamide dimethyl acetal (50 mL, 376 mmol) is refluxed under nitrogen for 8 hours. The reaction mixture is cooled and the solid collected by filtration to yield product (5) as an orange solid (37.2 g, 160 mmol, 95%).

N-[3-[3-(Dimethylamino)-1-oxo-2-propenyl]-phenyl]-N-methylacetamide (6)

To a suspension of N-[3-[3-(dimethylamino)-1-oxo-2-propenyl]-phenyl]-acetamide (5) (22.07 g, 95 mmol) in anhydrous dimethylformamide (114 mL) under nitrogen in an ice bath is added sodium hydride (Aldrich, 60% in mineral oil) (4.75 g, 119 mmol) and, within 15 minutes, the gas evolution has ceased. To the above reaction mixture is added a solution of methyl iodide (Aldrich) (14.2 g, 99.8 mmol). The reaction mixture is stirred overnight and allowed to warm to room temperature. The reaction is triturated with hexane (3×150 mL) which is discarded. The reaction mixture is poured into ice water, extracted with dichloromethane (3×200 mL) which is dried with anhydrous sodium sulfate. The dry dichloromethane is concentrated to yield a solid, which is triturated with a solution of ethyl acetate and hexane (1:1, 200 m l). Product (6) is obtained as an orange solid (16.9 g, 68.6 mmol, 72%).

N-Methyl-N-[3-[3-(2-thienylcarbonyl)-pyrazolo[1,5-a]pyrimidin-7-yl]phenyl]acetamide (Compound 1 )

A mixture of (3-amino-1H-pyrazol-4-yl)-2-thienylmethanone (4) (1.93 g, 10 mmol) and N-[3-[3-(dimethylamino)-1-oxo-2-propenyl]-phenyl]-N-methylacetamide (6) (2.46 g, 10 mmol) in glacial acetic acid (100 mL) is refluxed for 8 hrs. Evaporation of all volatiles on a rotary evaporator gives a residue which is partitioned between aqueous saturated sodium bicarbonate and methylene chloride. The methylene chloride layer is dried over sodium sulfate and filtered. Two additional volumes of methylene chloride are added and the solution is warmed to reflux. Hexane is added until crystallization is observed. The mixture is cooled and filtered to give Compound 1 as a yellow solid (2.57 g, 7 mmol, 70%).

It will be appreciated that, although specific embodiments of the invention have been described herein for purposes of illustration, various modifications may be made without departing from the spirit and scope of the invention. Accordingly, the invention is not limited except as by the appended claims.

What is claimed is:

1. N-methyl-N-(3-{3-[2-thienylcarbonyl]-pyrazol-[1,5-α]-pyrimidin-7-yl}phenyl)acetamide or a pharmaceutically acceptable salt thereof.

2. A composition comprising N-methyl-N-(3-{3-[2-thienylcarbonyl]-pyrazol-[1,5-α]-pyrimidin-7-yl}phenyl) acetamide or a pharmaceutically acceptable salt thereof and a pharmaceutically acceptable carrier.

3. The composition of claim 2, wherein the composition is formulated for oral administration.

4. The composition of claim 3 wherein the composition is in the form of a pill, capsule or tablet.

5. The composition of claim 2 in dosage unit form comprising from 0.1 to 250 mg of N-methyl-N-(3-{3-[2-thienylcarbonyl]-pyrazol-[1,5-α]-pyrimidin-7-yl}phenyl) acetamide.

6. A method for treating insomnia in a patient in need thereof, comprising administering to the patient an effective amount of N-methyl-N-(3-{3-[2-thienylcarbonyl]pyrazol-[1,5-α]-pyrimidin-7-yl}phenyl)acetamide or a pharmaceutically acceptable salt thereof.

7. A method for inducing sleep in a patient in need thereof, comprising administering to the patient an effective amount of N-methyl-N-(3-{3-[2-thienylcarbonyl]-pyrazol-[1,5-α]-pyrimidin-7-yl}phenyl)acetamide or a pharmaceutically acceptable salt thereof.

8. A method for inducing sedation or hypnosis in a patient in need thereof, comprising administering to the patient an effective amount of N-methyl-N-(3-{3-[2-thienylcarbonyl]-pyrazol-[1,5-α]-pyrimidin-7-yl}phenyl)acetamide or a pharmaceutically acceptable salt thereof.

9. A method for inducing skeletal muscle relaxation in a patient in need thereof, comprising administering to the patient an effective amount of N-methyl-N-(3-{3-[2-thienylcarbonyl]-pyrazol-[1,5-α]-pyrimidin-7-yl}phenyl) acetamide or a pharmaceutically acceptable salt thereof.

* * * * *